United States Patent
McGown

(10) Patent No.: US 8,622,873 B2
(45) Date of Patent: Jan. 7, 2014

(54) EXERCISE EQUIPMENT USAGE MONITORING METHOD AND APPARATUS

(76) Inventor: Rhoderick Euan McGown, Edinburgh (GB)

( * ) Notice: Subject to any disclaimer, the term of this patent is extended or adjusted under 35 U.S.C. 154(b) by 510 days.

(21) Appl. No.: 12/844,221

(22) Filed: Jul. 27, 2010

(65) Prior Publication Data

US 2011/0059825 A1 Mar. 10, 2011

(30) Foreign Application Priority Data

Jul. 27, 2009 (GB) .................................. 0913029.5
Feb. 1, 2010 (GB) .................................. 1001510.5

(51) Int. Cl.
*A63B 24/00* (2006.01)

(52) U.S. Cl.
USPC .................. 482/1; 482/8; 482/9; 482/901

(58) Field of Classification Search
USPC .......... 482/1, 8, 148, 901, 902; 340/4.6, 4.61, 340/4.62; 701/29.3; 705/7.12, 7.24, 7.25, 705/28

See application file for complete search history.

(56) References Cited

U.S. PATENT DOCUMENTS

| | | | |
|---|---|---|---|
| 6,059,692 A | 5/2000 | Hickman | |
| 6,638,198 B1 * | 10/2003 | Shea | 482/8 |
| 6,656,091 B1 | 12/2003 | Abelbeck et al. | |
| 6,783,482 B2 * | 8/2004 | Oglesby et al. | 482/54 |
| 6,949,052 B2 * | 9/2005 | Millington et al. | 482/8 |
| 7,062,183 B2 * | 6/2006 | Maeyama et al. | 399/45 |
| 7,621,846 B2 * | 11/2009 | Ainsworth et al. | 482/8 |
| 8,128,532 B2 * | 3/2012 | Chen et al. | 482/8 |
| 2004/0229730 A1 | 11/2004 | Ainsworth et al. | |
| 2005/0010426 A1 | 1/2005 | Chen et al. | |
| 2005/0240417 A1 | 10/2005 | Savage | |
| 2007/0033069 A1 * | 2/2007 | Rao et al. | 705/2 |
| 2007/0219059 A1 * | 9/2007 | Schwartz et al. | 482/8 |
| 2008/0015087 A1 | 1/2008 | Negrin | |
| 2008/0077620 A1 | 3/2008 | Gilley et al. | |
| 2009/0023556 A1 | 1/2009 | Daly et al. | |

FOREIGN PATENT DOCUMENTS

| | | |
|---|---|---|
| EP | 1 188 460 | 3/2002 |
| EP | 2 153 875 | 2/2010 |
| WO | WO 2006/087738 | 8/2006 |
| WO | WO 2009/034307 | 3/2009 |

OTHER PUBLICATIONS

UK Search Report for GB1001510.5, dated Jul. 5, 2010.
Examination Report dated Apr. 18, 2013 issued in corresponding GB Application No. GB1001510.5.

* cited by examiner

*Primary Examiner* — Glenn Richman
(74) *Attorney, Agent, or Firm* — Nixon & Vanderhye PC

(57) ABSTRACT

A method of monitoring the use of exercise equipment at an exercise facility having a plurality of items of exercise equipment, the method comprising the steps of: providing a plurality of usage monitors, each associated with an item of exercise equipment, monitoring the usage of the plurality of items of exercise equipment concurrently using the usage monitors, and thereby calculating, for at least some of the items of exercise equipment, a measure of the proportion of the period of time during which respective items of exercise equipment are used. In some embodiments, the usage monitors can detect when an item of exercise equipment is occupied, even if it is not being operated, for example using a heat sensor. A graphical representation may be prepared of the usage of items of exercise equipment at each of a plurality of locations within the exercise facility.

20 Claims, 8 Drawing Sheets

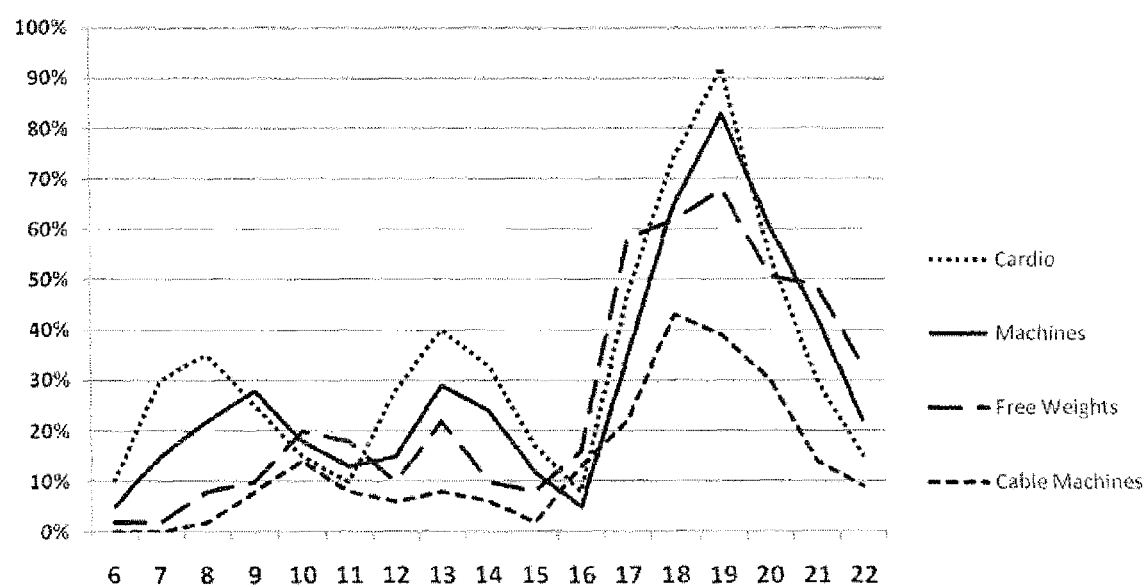
Figure 7 - % Usage Over the Course of a Day

|  |  | Cost | Hours used | Cost / hour |
|---|---|---|---|---|
| Rowing machine | 1 | £400 | 30 | £13 |
| Reclining cycling | 1 | £1,000 | 54 | £19 |
| Upright cycling | 1 | £900 | 32 | £28 |
| Cross trainer | 1 | £2,000 | 52 | £38 |
| Treadmill type 2 | 1 | £1,500 | 38 | £39 |
| Treadmill | 1 | £2,000 | 48 | £42 |
| Power plate | 1 | £4,000 | 60 | £67 |
| Shoulder cycling | 1 | £850 | 10 | £85 |
| Skiing machine | 1 | £2,200 | 22 | £100 |
| Stair climber | 1 | £500 | 5 | £100 |

Figure 8A

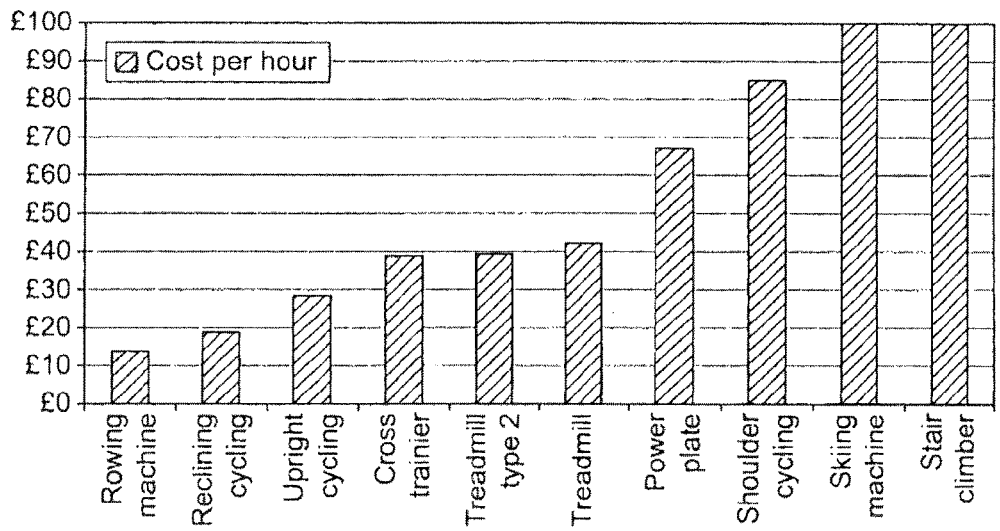

Figure 8B

|  | No. of machines | % of capacity | Minutes used | % time total usage |
|---|---|---|---|---|
| Treadmill | 1 | 10% | 48 | 14% |
| Cross trainer | 1 | 10% | 52 | 15% |
| Treadmill type 2 | 1 | 10% | 38 | 11% |
| Upright cycling | 1 | 10% | 32 | 9% |
| Rowing machine | 1 | 10% | 30 | 9% |
| Skiing machine | 1 | 10% | 22 | 6% |
| Reclining cycling | 1 | 10% | 54 | 15% |
| Power plate | 1 | 10% | 60 | 17% |
| Shoulder cycling | 1 | 10% | 10 | 3% |
| Stair climber | 1 | 10% | 5 | 1% |
| Total | 10 | 100% | 351 | 100% |

Figure 9A

EXERCISE EQUIPMENT USAGE MONITORING METHOD AND APPARATUS

FIELD OF THE INVENTION

The invention relates to exercise equipment and methods to monitor and measure the usage of items of exercise equipment within an exercise facility.

BACKGROUND TO THE INVENTION

In recent years, personal fitness and general good health have been brought to the forefront of the public consciousness. As a result exercise facilities, such as gymnasiums, have seen an increase in demand for their services, putting greater pressures on them to provide the products which the public want. Each gymnasium has only a limited amount of floor space within which they can make various items of exercise equipment available for their members. As a result a high priority for the gymnasium owners is to ensure that they provide the right number of the right items of exercise equipment within the space they have available. Therefore it is desirable to provide a solution which enables gymnasium owners to maximise use of equipment and the floor space they have, and to increase customer satisfaction by providing the equipment which the users of gyms and other exercise facilities prefer.

Some methods of monitoring exercise equipment in other ways to those described below and for other purposes are known. These include providing feedback to the user on user performance (U.S. Pat. No. 6,059,692, Hickman), a monitoring and billing means (U.S. Pat. No. 6,656,091 B, Abelbeck et al.; US 2005240417, Savage) and a method of predicting when equipment maintenance will be required (WO 2006087738 A, Camax S.A.). These methods provide the facility owners with data, such as which item of exercise equipment is used by which customer, but does not give them accurate data on the proportion of time for which a machine is occupied and therefore not available for other customers, whether or not it is in use. If a machine is occupied but not in use, it is unavailable for other gymnasium members and this occupancy period should ideally be taken into account when determining the selection of items of exercise equipment provided within an exercise facility.

Additionally, the above mentioned methods do not provide data concerning usage at specific times of the day or details of the specific types of exercise equipment used. It would be advantageous to provide improved apparatus and methods for collecting usage data which is more useful to the proprietors of exercise facilities to make resource allocation decisions.

Same aspects of the current invention aim to overcome these problems by providing an exercise equipment monitoring method and apparatus to record data including the usage and occupancy time for each item of exercise equipment over a limited time period, reducing the cost and inconvenience of the total monitoring process.

SUMMARY OF THE INVENTION

According to a first aspect of the invention there is provided a method of monitoring the use of exercise equipment at an exercise facility, having a plurality of items of exercise equipment, the method comprising the steps of: providing a plurality of usage monitors, each usage monitor associated with an item of exercise equipment and operable to detect whether the respective item of exercise equipment is being operated at a given time; monitoring the usage of the said plurality of the items of exercise equipment using the said usage monitors, and thereby calculating, for at least some of the items of exercise equipment, a measurement related to the proportion of a period of time during which one or more respective items of exercise equipment are used.

Thus, it is possible to measure the demand customers put on the equipment through the usage monitors, enabling gym operators to adjust their equipment capacity to match their customer demand profile. This increases the utilisation of the equipment.

It also increases customer satisfaction as it enables the operators of exercise facilities to provide more of the types of equipment that customers like and less of the equipment that they do not like.

Typically, the usage of the said plurality of items of exercise equipment is monitored concurrently using the said usage monitors.

It may be that the calculated measurement related to the proportion of the period of time during which one or more respective items of exercise equipment are used is a measurement related to the proportion of the period of time during which the one or more respective items of exercise equipment are operated.

However, preferably, at least some of the said usage monitors are operable to detect whether a user is occupying the respective item of exercise equipment at a given time and the calculated measurement related to the proportion of the period of time during which one or more respective items of exercise equipment are used is related to the proportion of the period of time during which the one or more respective items of exercise equipment are either or both operated and occupied.

By detecting whether a user is occupying the respective item of exercise equipment we refer to detecting whether a user is occupying the respective item of exercise equipment by a method which is able to detect occupation of the one or more respective items of exercise equipment independently of whether it or they are being operated.

The calculated measurement related to the proportion of the period of time during which the one or more respective items of exercise equipment are used (e.g. operated, or either or both operated and occupied, as appropriate) may be a measure of the period of time during which the one or more respective items of exercise equipment are not in use (e.g. not operated, or neither operated nor occupied, as appropriate).

The period of time may be longer than a day. However, the period of time may be a portion of day, for example, an hour. The method may comprise calculating an average (e.g. mean, median or mode) of measurements taken during the same period of time on a plurality of different days. Preferably, the method comprises the step of calculating averages of measurements taken on a plurality of different days at each of a plurality of different times to prepare a profile of average use at different times of day. This enables the proprietor of an exercise facility to identify times of peak use and to take into account average use at peak times.

The calculated measurements may concern a single item of exercise equipment. However, preferably, the method comprises the step of calculating measurements related to the proportion of a period of time during which one or more of a group of a plurality of items of exercise equipment are used, or the average proportion of the items of exercise equipment within a group which are used (typically concurrently). A group of a plurality of items of exercise equipment may be a group of items of exercise equipment with equivalent function (e.g. rowing machines, biceps curl resistance machines, lateral pulldown machines etc.). However, a group of a plurality of items of exercise equipment may be a group of items of items of exercise equipment which fall into a particular category (e.g. cardiovascular exercise machines, resistance machines) or a group of items of exercise equipment which are located close to each other. The items of exercise equipment may comprise one or more of cardiovascular exercise machines and resistance machines.

The calculated measurement may relate to the proportion of time at least one of the items of exercise equipment in a group of items of exercise equipment are used (e.g. operated, or either or both operated and occupied), or the proportion of time at least one of the items of exercise equipment in a group of items of exercise equipment is not used (e.g. not operated, or neither operated nor occupied). This enables a proprietor of an exercise facility to determine for what proportion of a period of time at least one item of exercise equipment in a group of items is available for use.

The calculated measurement may be related to the available capacity of items of exercise equipment in a particular group (e.g. of a particular type) provided in the exercise facility. For example, the calculated measurement may be a function of (e.g. proportional to) the proportion of a period of time during which one or more respective items of exercise equipment are used (e.g. operated, or either or both operated and occupied, as appropriate) and a function of (e.g. inversely proportional to) the proportion of the items of exercise equipment provided in the exercise facility represented by the said one or more respective items of exercise equipment. The method may comprise the step of calculating a measure of the relative usage (e.g. operated, or either or both operated and occupied, as appropriate) of the one or more respective items of exercise equipment relative to the proportion of the items of exercise equipment provided in the exercise facility represented by the said one or more respective items of exercise equipment. The calculated measurement may be related to the proportion of the period of time during which the one or more respective items of exercise equipment would have been used if all of the items of exercise equipment which have usage monitors associated therewith were used for equal periods of time.

The calculated measurement may be related to the location of individual items or groups of items of exercise equipment. Thus, a calculated measurement may concern the proportion of a period of time during which items of exercise equipment at each of a plurality of locations within the exercise facility are used. The method may comprise the step of receiving the position of an item of exercise equipment, calculating occupancy and usage from data received from the item of exercise equipment and using the position of the item of exercise equipment to calculate a map of the usage, occupancy or both usage and occupancy of items of exercise equipment by position. The position of items of exercise equipment may be obtained by manually entering position data, measuring the position of individual items of exercise equipment, for example by measuring the location of the respective usage monitor. The usage monitor may comprise a position monitor. The map may be calculated for either individual items of exercise equipment or for groups of items of exercise equipment, for example grouped together by type of exercise equipment.

The map may represent usage or occupancy of items of exercise equipment by a contour plot or "heat map" colouring scheme in which portions of a diagram of the exercise facility, or part thereof, are coloured according to usage of items of exercise equipment at that location. Such a representation of the calculated data would allow areas of high usage or occupancy to be readily and intuitively determined. The map is typically displayed by way of a screen.

Preferably, a user interface is provided, the user interface comprising a screen operable (under control of a program executed on a computer) to display a graphical representation of the proportion of a period of time that one or more items of exercise equipment are used, arranged on screen according to type or location within the exercise facility.

Typically, the graphical representation comprises a plurality of graphical icons. Each item of exercise equipment within the exercise facility may be represented by a graphical icon. A graphical icon may represent a plurality of items of exercise equipment within the exercise facility. Each type of exercise equipment within the exercise facility may be represented by a graphical icon. Therefore, graphical icons may represent one or more items of exercise equipment.

Each graphical icon within the plurality of graphical icons may indicate the usage of the one or more items of exercise equipment that each graphical icon represents. The colour of each graphical icon within the plurality of graphical icons may represent the usage of the one or more items of exercise equipment. For example, blue may indicate low usage, green may indicate medium usage and red may indicate high usage. Alternatively, a smooth spectrum of colours may be used to allow a continuous scale of values of usage to be displayed.

The relative size of the graphical icons within the plurality of graphical icons may represent the usage of the one or more items of exercise equipment. For example, a small graphical icon may represent low usage and a large graphical icon may represent high usage.

Both the relative size and colour of the graphical icons within the plurality of graphical icons may represent the usage of the one or more items of exercise equipment.

The said period of time may be a part of a day. The proportion of the period of time is typically sampled over a plurality of days and is typically averaged. The said period of time may be user selectable. In some embodiments, the screen displays a graphical representation of the proportion of the period of time that one or more items of exercise equipment are used, arranged on screen according to their type or location within the exercise facility and the said period of time changes with time, for example, progresses through some or all of the day.

The exercise facility is typically a gymnasium but may be a room or complex of rooms located within the same building and having the exercise equipment therein.

Typically the usage monitor comprises at least one sensor and a communication interface by which the data produced by the at least one sensor is transmitted to a data recorder.

A data recorder may be provided to receive data from a plurality of usage monitors, each of which is associated with one of a plurality of items of exercise equipment. Some or all of the usage monitors may further comprise a data logger that locally stores data produced by the at least one sensor. The data logger may comprise a clock and be operable to time stamp the data produced by the at least one sensor. The data logger may further comprise a communication interface operable to transmit stored data from the data logger to a said data recorder which data recorder is operable to receive, record, and typically also process, data from a plurality of usage monitors. The communication interface may be a wired or wireless communication interface.

Preferably, the at least one sensor is operable to detect whether an item of exercise equipment is occupied. At least one sensor may be operable to detect whether an item of exercise equipment is being operated. The same at least one sensor may be operable to detect whether an item of exercise equipment is being operated and, independently, whether the item of exercise equipment is being occupied.

Typically, the sensor type will be dependent on the type of the item of exercise equipment to be monitored using that sensor. For items of equipment where a saddle or seat is provided, such as cycling or rowing machines, a heat sensor, such as a thermocouple, located in or on the saddle may be employed to detect the body of the user if they are seated on the equipment, and so record the device occupancy. For items of equipment with parts which move when the equipment is in operation, such as resistance machines, one or more of an accelerometer, a gyroscope and a vibration sensor can be used to detect the motion and thereby sense that the item of equipment is being operated. With appropriate data processing apparatus one or more of an accelerometer, a gyroscope and a vibration sensor can be used to discern vibrations causes by a person sitting a seat of the item of exercise equipment and thereby occupying the item of equipment, even if the item of exercise equipment is not actually operated.

Typically, for items of exercise equipment which a user mounts, such as a treadmill, exercise bike or weights bench, the at least one sensor may comprise a load monitor, mounted such that the load on the item of exercise equipment may be measured. The at least one sensor may determine the occupancy of the item of exercise equipment by detecting a change in load. For example, an increase in measured load may indicate that the item of exercise equipment has become occupied, and a decrease in measured load may indicate that the item of exercise equipment has become unoccupied. Alternatively, there may be set a threshold load above which the item of exercise equipment is determined to be occupied. The at least one sensor may be mounted directly beneath the item of exercise equipment or beneath the surface the item of exercise equipment is itself mounted upon. The at least one sensor may be a pressure sensor.

Preferably, the or each usage monitor is demountably retrofittable to standard exercise equipment, without the standard exercise equipment needing to be modified, such that the usage monitor can be detached, after sufficient data has been collected for example. Thus, the method may comprise providing a plurality of items of exercise equipment already within the exercise facility with a usage monitor. However, the usage monitor may be integrated permanently into the item of exercise equipment and so the method may comprise providing a plurality of items of exercise equipment with integral usage monitors at the exercise facility.

According to a second aspect of the invention there is provided a usage monitor for monitoring the usage of exercise equipment, the usage monitor comprising at least one sensor and a communication interface.

At least one said sensor may be an occupancy sensor operable to determine whether an item of exercise equipment is being occupied.

At least one said sensor may be an operation sensor operable to determine whether an item of exercise equipment is being operated.

At least one said sensor may be operable to determine whether an item of exercise equipment is being occupied and operated.

The communication interface may be a wired or wireless interface operable to communicate electronically with a data recorder, which may be portable. Typically, the data recorder is a computer operable to receive data from the usage monitor by way of a wireless or wired communication interface and to record and analyse data received, and display calculated measurements to a user.

Preferably the usage monitor is demountably attachable to an item of exercise equipment. However, the usage monitor may be integral to the item of exercise equipment. The usage monitor may comprise a fixture for demountably attaching the usage monitor to an item of exercise equipment.

According to a third aspect of the invention there is provided a system (for example, apparatus) comprising a plurality of usage monitors according to the second aspect of the invention, each of which is attached to a respective item of exercise equipment, and a computing device operable to receive data from each of the plurality of usage monitors and calculated measurements related to the proportion of a period of time during which one or more respective items of exercise equipment are used.

Preferably, the plurality of usage monitors are operable to time stamp data as it is recorded.

Preferably, some or all of the plurality of usage monitors are demountably attachable to a respective item of exercise equipment. Nevertheless, some or all of the plurality of usage devices may be integral to an item of exercise equipment.

The data from some of the plurality of usage monitors may be grouped. For example, the data may be grouped by type of exercise equipment from which the data is recorded.

In addition, the data may be analysed to reveal information pertaining to exercise equipment usage at peak times of the day, for example, between the hours of 5 and 7 pm during the week. Data analysed by this method may enable the capacity of exercise equipment within a facility to better match the demand.

The system may further comprise a user interface, such as a display and one or more input peripherals (e.g. a keyboard, touch screen interface, a mouse or other pointing device) to enable a user to carry out one or more functions selected from: inputting data concerning the items of exercise equipment provided at the exercise facility, group items of exercise equipment, and selecting visual presentations of calculated data concerning usage of items, or groups of items, of exercise equipment.

According to a fourth aspect of the present invention there is provided an item of exercise equipment comprising a usage monitor operable to determine whether the item of exercise equipment is being either or both operated and occupied, the monitor comprising a sensor which is operable to determine whether the item of exercise equipment is being occupied independently of whether it is being operated.

The usage monitor may also comprise a sensor which is operable to determine whether the item of exercise equipment is being operated. The usage monitor may be demountably attachable to the item of exercise equipment. The usage monitor may be integral to the item of exercise equipment. The sensor may be a heat sensor, for example a thermocouple or an infra-red camera.

Optional features described in relation to any one of the four aspects of the invention are optional features of any of the four aspects of the invention.

DESCRIPTION OF THE DRAWINGS

An example embodiment of the present invention will now be illustrated with reference to the following Figures in which:

FIG. 7 is a graph illustrating the usage of different groups of items of exercise equipment during the course of a day;

FIGS 8A and 8B illustrate the cost per hour of use of items of exercise equipment;

FIGS 9A, 9B and 9C illustrate example graphical outputs showing equipment usage relative to capacity.

DETAILED DESCRIPTION OF AN EXAMPLE EMBODIMENT

Figure 1:
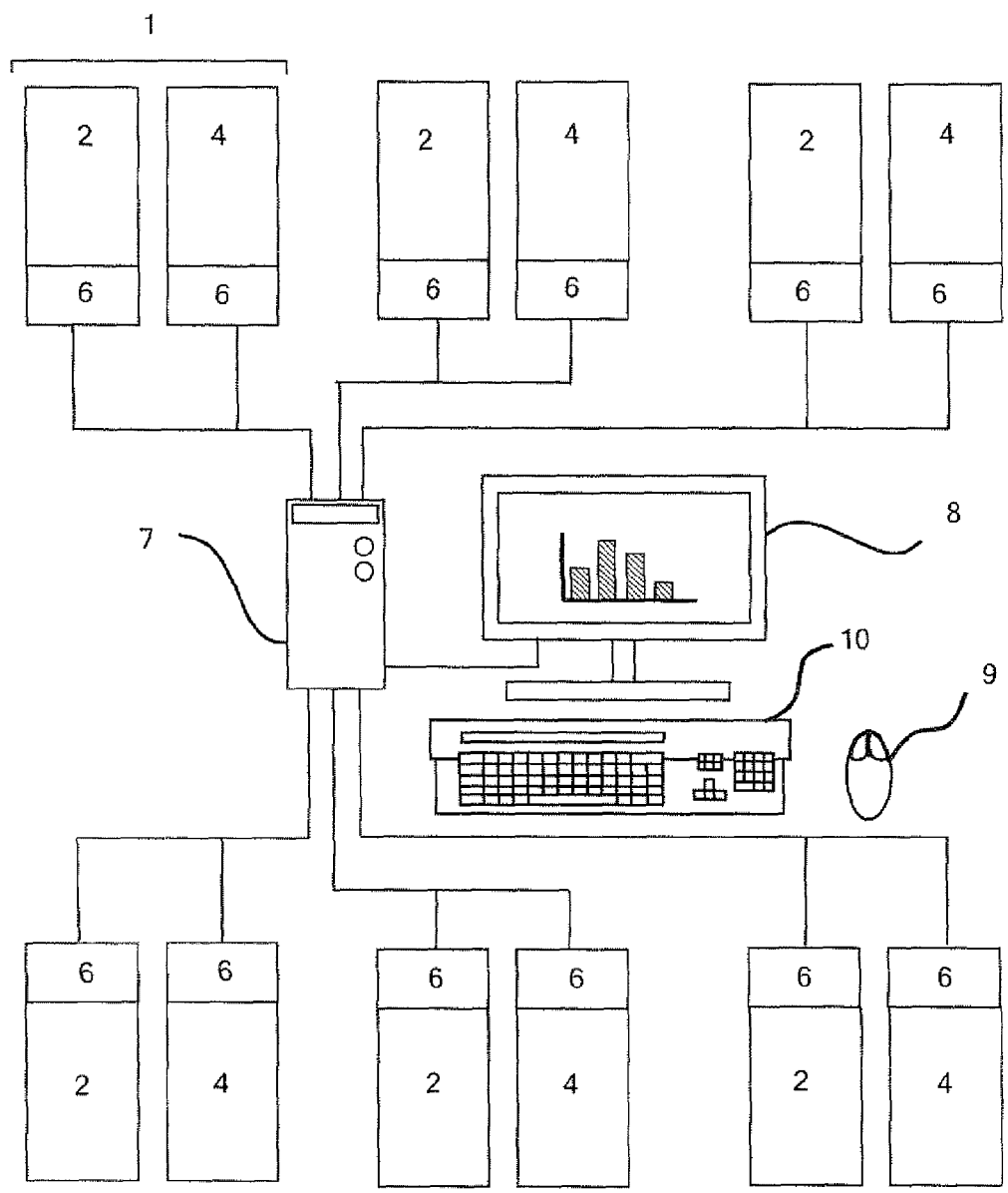
FIG. 1 is a schematic diagram of a usage monitor.
Figure 2:
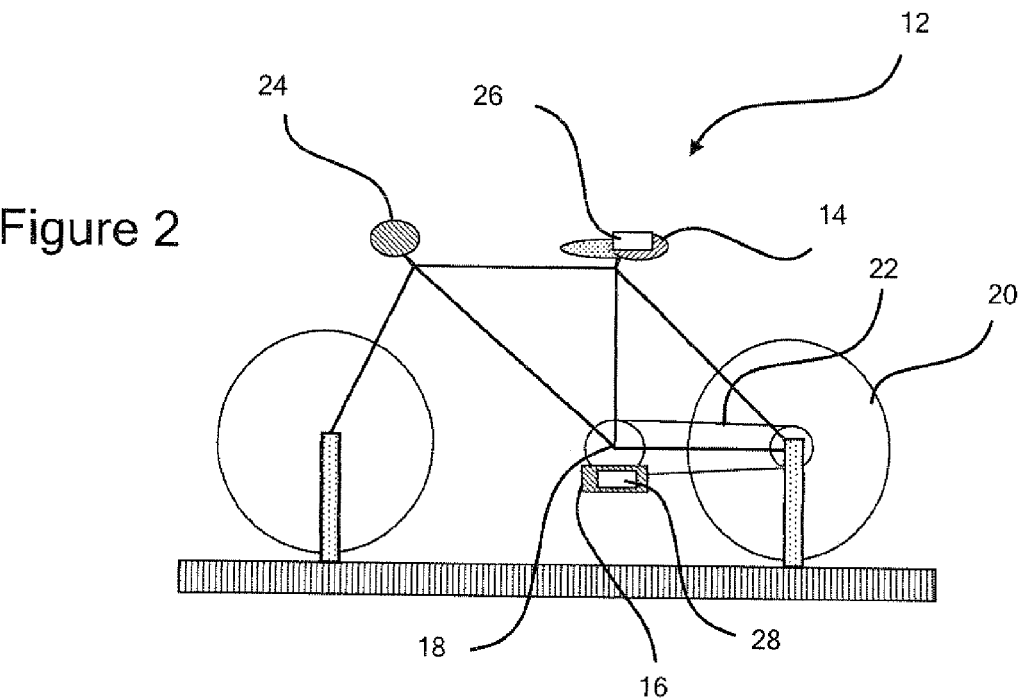
FIG. 2 is a side view of an exercise bike having a usage monitor according to the invention.
Figure 3:
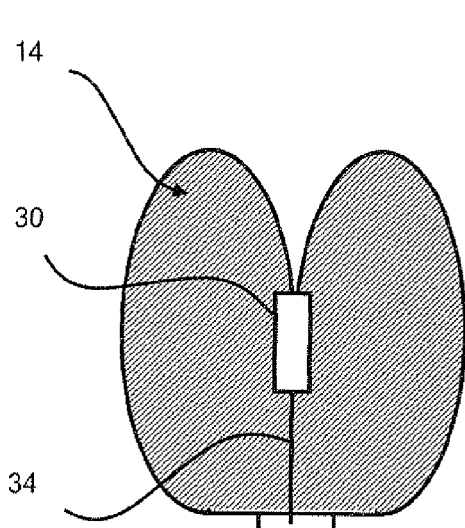
FIG. 3 is a plan view of the saddle of the exercise bike having a usage monitor according to the invention.
Figure 4:
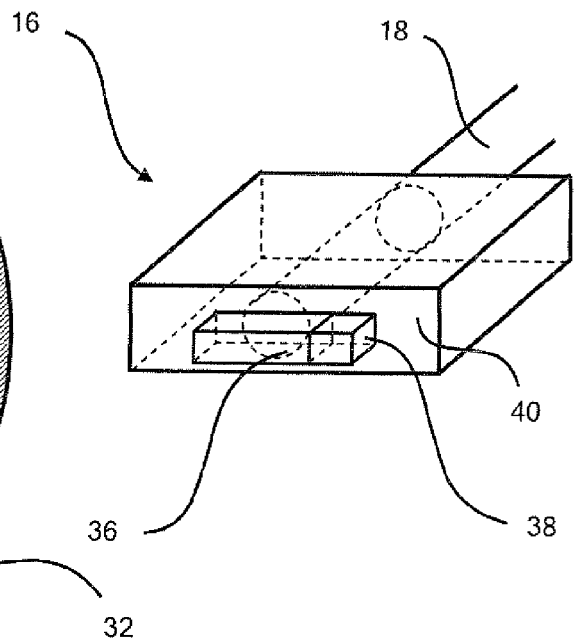
FIG. 4 is a perspective view of an exercise bike pedal with the operation monitor attached.

With reference to FIGS. 1 to 5, a usage monitor 1 for monitoring the usage of exercise equipment comprises an occupancy sensor 2, an operation sensor 4, a communication interface 6 and a fixture, and a plurality of said usage monitors comprising a network communicating electronically with a central recording system comprising a computer 7, a display 8, and user input peripherals such as a mouse 9 and keyboard 10.

The described first embodiment is for a usage monitor monitoring an exercise bike 12 in a gymnasium, but similar usage monitors can applied to any item of exercise equipment. The fixture can be a an adhesive pad, a magnet, one or more apertures for receiving a strap, or a strap which is integral to the usage monitor The exercise bike comprises a saddle 14, a pair of pedals 16 mounted around a single axle 18 such that they may rotate about the single axle, a wheel 20 connected to the single axle by a linkage 22 such that rotation of the single axle is coupled to rotation of the wheel, and a pair of handle bars 24. The exercise bike will be understood to be occupied when a user is sitting on the saddle and the exercise bike will be understood to be in operation if the pedals are being driven around the axle. The user may rest their arms or hands on the pair of handle bars whilst the exercise bike is being occupied or in operation.

A usage monitor for the exercise bike comprises two discrete units; an occupancy monitor 26 and an operation monitor 28.

The occupancy monitor comprises a heat sensor 30, such as a thermocouple, reversibly mounted underneath the upper surface of the saddle such that the heat sensor is in thermal contact with the upper surface of the saddle and in electrical contact with communication interface 32. The heat sensor is attached to the communication interface via a wire 34 such that the communication interface is mounted underneath the saddle. The heat sensor detects the body heat of a user when the user is sat on the saddle and the resulting data is time stamped and sent via the communication interface to a remote data recording system for analysis.

The operation monitor comprises an accelerometer 36 and a communication interface 38 reversibly attached to the side of one of the pedals 40 on the far side of the axle 18. The accelerometer detects the acceleration of the pedals as they are driven around the axle and the data produced is sent via the communication interface to a remote data recording system where the data is time stamped and analysed.

In both the operation monitor and the occupation monitor, the communication interface may be a wired connection, for example a USB 2.0 or FireWire IEEE-1394a connection, or a wireless connection such as an IR transmitter, Wi-fi or Bluetooth IEEE Standard 802.15.1.

Figure 5:
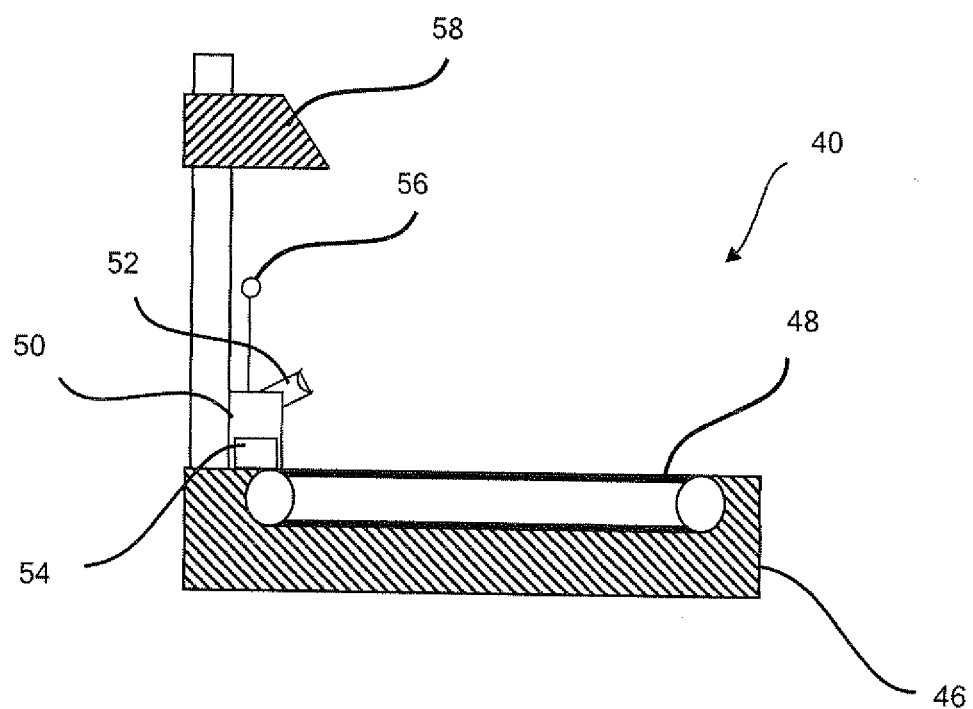
FIG. 5 is a side view of a treadmill with a usage monitor according to the invention.

The usage monitor is most effective when a plurality of usage monitors are used with a plurality of items of exercise equipment concurrently within a single exercise facility. FIG. 5 illustrates a usage monitor monitoring the use of a treadmill in a gymnasium.

A treadmill 40 comprises a controller means 54, a base 46 and a surface which may be controllably revolvable 48 such that a user can run on the surface whilst remaining stationary. When a treadmill is operated the revolving of the surface produces vibrations of the base, vibrations that are accentuated when a user runs on said surface.

A usage monitor 50 for the treadmill comprises a single unit comprising an occupancy sensor 52, an operation sensor 54 and a communication interface 56. The occupancy sensor is an infra-red sensor operable to detect a body emitting infra-red radiation, such as a user, within the range of the infra-red sensor. The usage monitor is positioned on the treadmill such that the infra-red sensor may detect a user when they occupy the treadmill, whether they are sitting, standing or running on the treadmill. The operation sensor is an accelerometer operable to detect the vibrations of the base produced when the treadmill is in operation. The usage monitor is positioned on the treadmill such that the accelerometer is in contact with the base.

Data produced by the operation sensor and the occupation sensor is transmitted to a data recorder via the communication interface which may be a wired connection, for example a USB 2.0 or FireWire IEEE-1394a connection, or a wireless connection such as an IR transmitter, Wi-fi or Bluetooth IEEE Standard 802.15.1.

The data recorder may be a computer comprising a communication interface, a data storage device, a processor, a display device, such as a monitor and user input peripherals, such as a keyboard and a pointing device. Data may be stored by the usage monitors and then retrieved periodically by the data recorder, for example, by a user carrying the remote recording system around the exercise facility. In some embodiments, the usage monitors can communicate continuously or periodically with the data recorder and so it is not essential for the usage monitors to store data locally. Typically, usage data (such as whether an item of exercise equipment is being occupied and whether an item of exercise equipment is being operated at a given time) is stored with reference to the time at which that data was measured. A time stamp may be applied by the usage monitor or, if data is relayed quickly to the data recorded, the data recorder can store the data with reference to the time at which it is received by the data recorded.

Generally, usage data is stored with reference to the position of the item of exercise equipment the usage data originates from.

The processor is operable to analyse the data received from a plurality of usage monitors and to prepare appropriate output. Statistics may be presented concerning the proportion of a period of time that an item of exercise equipment is used (e.g. operated or occupied) or the period of time that the item of exercise equipment is not used (e.g. neither operated nor occupied). The ability of the usage monitors to measure whether an item of exercise equipment is being occupied, whether or not it is being operated, means that the resulting data is of more practical use to the proprietor of the exercise facility than if the usage monitors only measured whether an item of exercise equipment is being operated. Statistics can be calculated concerning the proportion of a group of items of exercise equipment which are being used, or the period of time that at least one of a group of items of exercise equipment are used, or the period of time that least one of a group of items of exercise equipment are not being used.

In some embodiments, the processor is operable to analyse the positional data and usage data to calculate a data map whereby the pattern of usage by location may be determined. The data map typically comprises a two dimensional representation of the exercise facility divided into areas containing specific exercise equipment, for example, an area containing treadmills. The areas of the data map may be sub-divided to show the positions of individual items of exercise equipment. The areas or sub-divided areas are generally colour coded depending on the relative usage of items of exercise equipment within the respective area or sub-divided area.

FIG. 6 illustrates example graphical output displayed on a monitor concerning two example measurements related to the proportion of a period of time during which one or more respective items of exercise equipment are used. A user may select a period of time using selectable user interface elements 60, for example using a computer mouse. For example, a user might select the period of time from 1700 to 1900 during week days. The proportion of the selected period of time of day, averaged over the selected days, for which each individual item of exercise equipment in an exercise facility is used (e.g. operation, or preferably either or both operation or occupation) may be displayed as a percentage. A user may select an alternative option and view the same data expressed as a proportion of the selected period of time of day for which the same individual items of exercise equipment are unused.

Rather than presenting data concerning the usage of individual items of exercise equipment, the computer may present statistics concerning the usage of groups of items of exercise equipment, for example, the proportion of time that at least one treadmill or exercise bike, or another type of exercise machine, is available. This is of practical importance as the period of time during which none of a category of machine is available is significant as this is the period of time during which a user cannot choose to carry out a particular type of exercise.

Figure 6A:
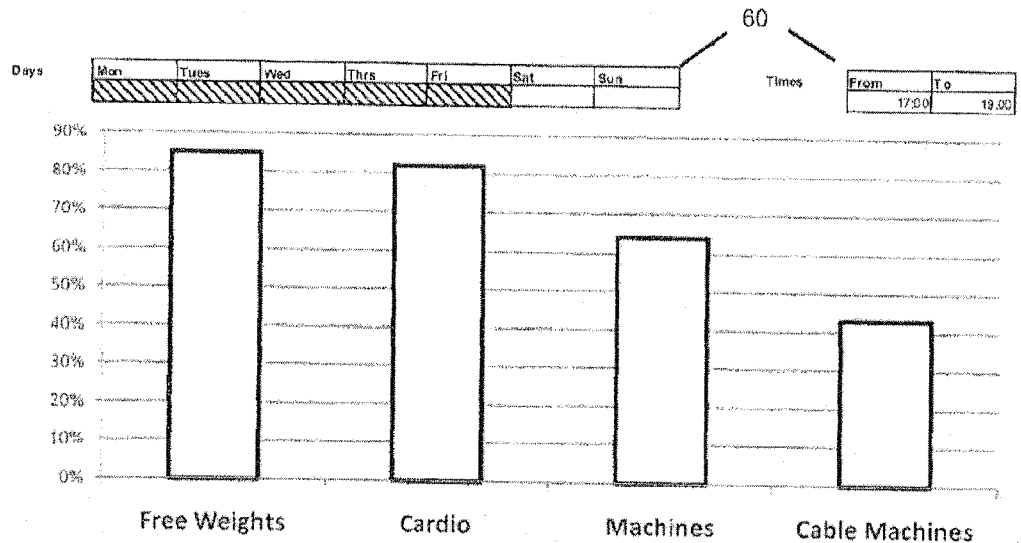
FIGS. 6A and 6B illustrates average percentage usage of groups of items of exercise equipment (FIG. 6A), and more detailed information of usage of individual items of exercise equipment responsive to selection of one of the groups (FIG. 6B)
Figure 6B:
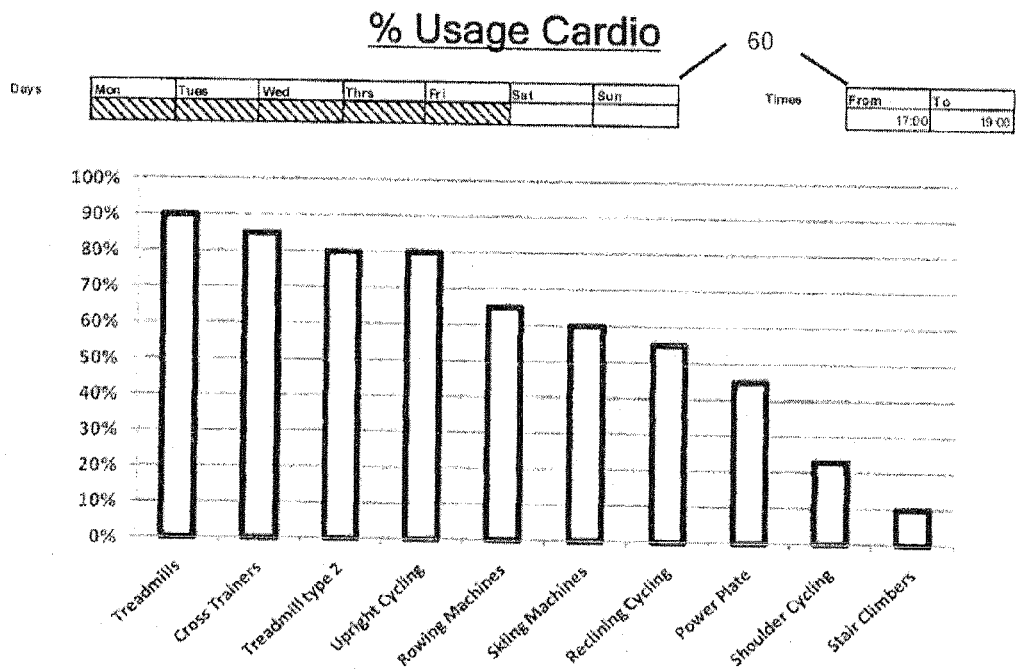

FIG. 6A illustrates output in which the average percentage usage (e.g. operation, or preferably either or both operation or occupation) of items of exercised equipment in four different user selected groups (free weights, cardio, machines, cable machines) is displayed using separate bars for each group. A user may select an individual group and view the usage of individual items of exercise equipment within the selected group. An example of a resulting image is shown in FIG. 6B.

Data concerning different periods of time may be presented together to provide an overview of usage (e.g. operation, or preferably either or both operation or occupation) over a longer period of time. For example, FIG. 7 illustrates a graph of example usage of the four different group of machines referred to in FIG. 6A at an exercise facility over the course of the day.

Data can also be calculated which takes into account the relative cost of different items of exercise equipment, or groups of items of exercise equipment. For example, FIGS. 8A and 8B include a chart of the cost of various example items of exercise equipment and the average number of hours for which each is used during a week and therefore calculates and average cost per hour for which the item is used, which is displayed in graphical format in FIG. 8B.

Figure 9B:
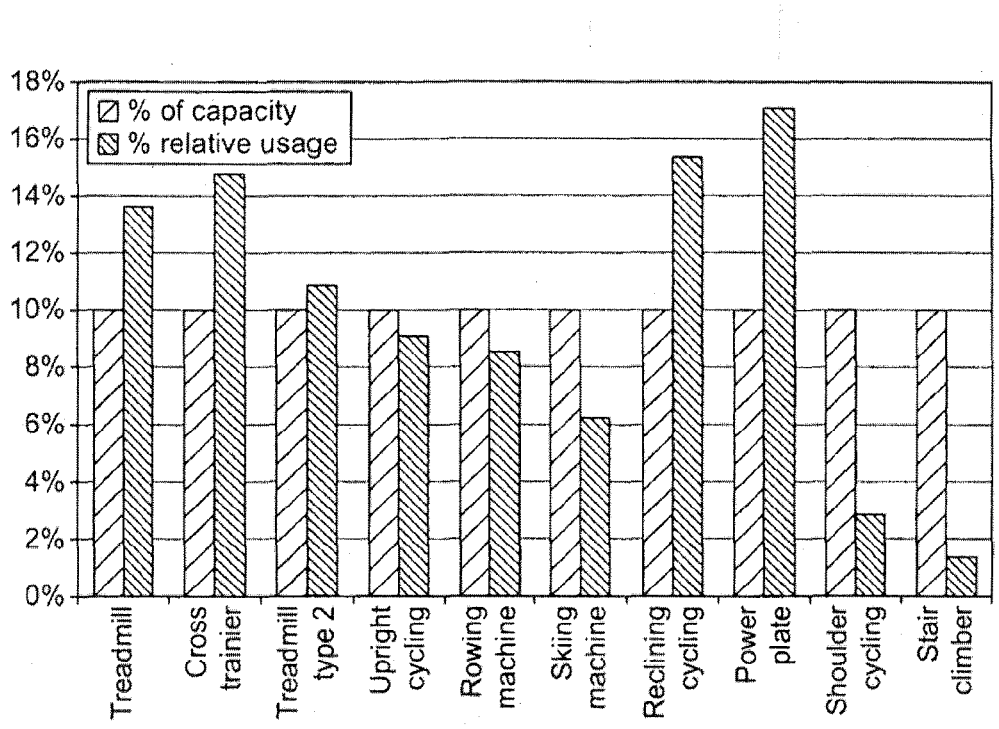
Figure 9C:
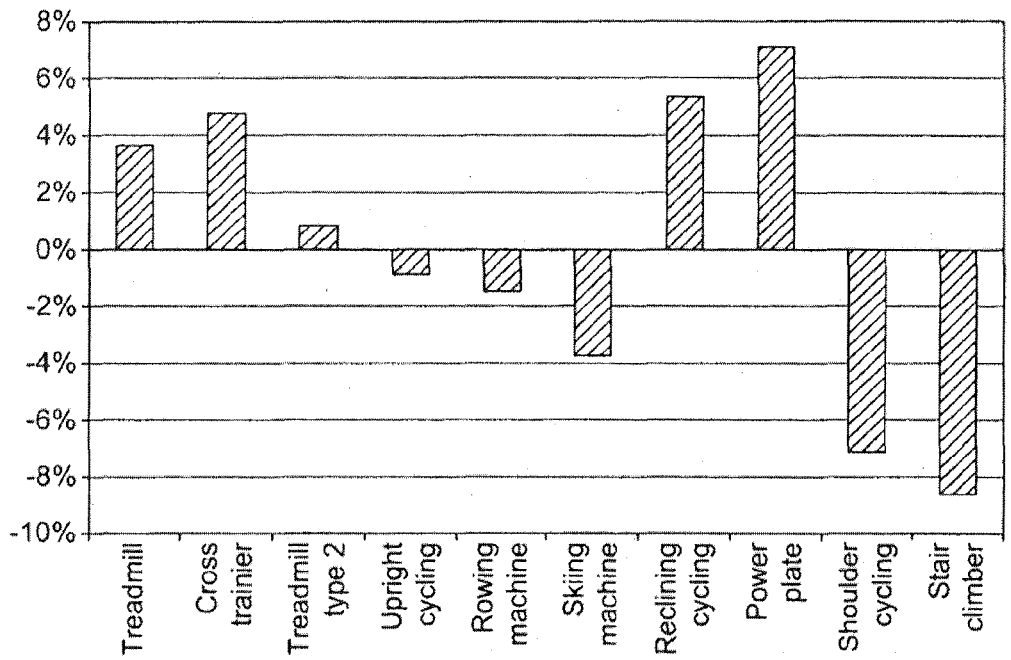

One presentation of the data that has been found to be of particular use is a chart, or other visual representation, which shows the proportion of a period of time in which an item of exercise equipment, or group of items of exercise equipment within a particular category, are occupied or operated, as a fraction of the sum of the amount of time for which all of the monitored items of exercise equipment at a facility, or a suitable subset thereof, are used. This measurement is shown as % relative usage in FIG. 9B. This is compared with the proportion of the total amount of the available capacity at the facility represented by the item of exercise equipment, or group of items of exercise equipment. This measurement is shown as % capacity in the FIG. 9B. The difference between these two measurements is also shown in FIG. 9C and this provides a useful visual representation of the proportion of a period of time for which one or more items or categories of item of exercise machine are in use relative to the availability of those items or categories of item. In effect exercise equipment with a positive difference between relative usage and capacity are those in highest demand, and exercise equipment with a negative difference between relative usage and capacity are those that are least in demand. Gymnasium owners may then better match the capacity of the exercise equipment available at their facility with demand.

Figure 10:
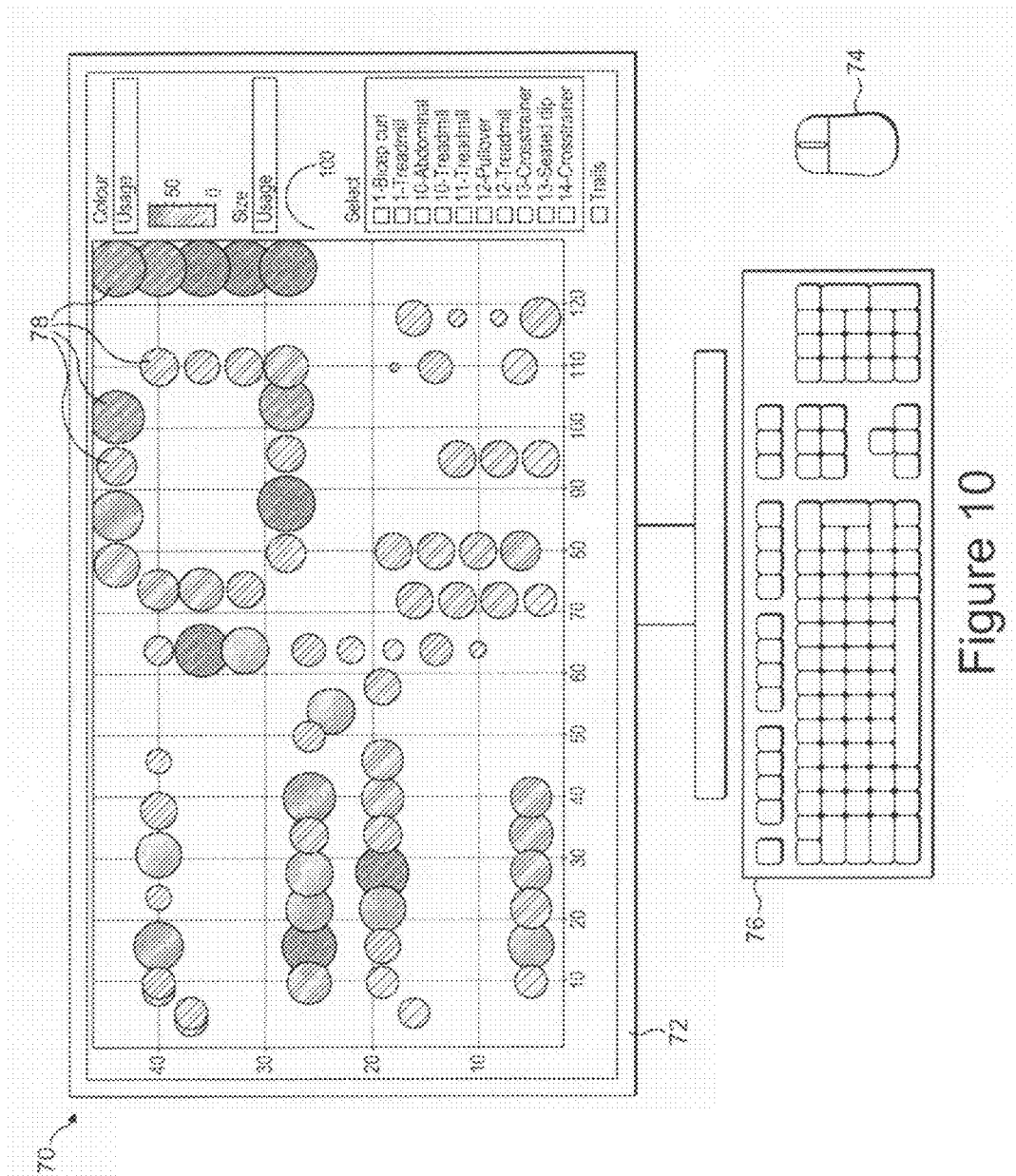
FIG. 10 illustrates an example graphical output showing equipment usage according to location.

With reference to FIG. 10 a user interface 70 comprises a display 72 operable to present to the user a graphical representation of the proportion of time that one or more items of exercise equipment are used arranged on screen according to their location within the exercise facility, and user input peripherals such as a mouse 74 and keyboard 76.

The graphical representation comprises a series of circular spots (acting as graphical icons) 78, each spot representing an item of exercise equipment within the exercise facility. The colour and size of each spot indicates the usage of the corresponding item of exercise equipment that each spot represents. In this embodiment, a blue, small spot represents an item of exercise equipment with low usage, and a red, large spot represents an item of exercise equipment with high usage. In another embodiment, a gray scale colour scheme could be used, with white representing low usage and black representing high usage.

In an embodiment, the colour and size of each spot represent usage (typically occupancy or operation) to period of time (for example, a half hour or one hour period) within a day, using data averaged over a number of days. A user can select an animation in which the period of time which the colour and size of each spot concerns changes between successive periods of time during the day. This has been found to be especially helpful in allowing the pattern of usage within a gym or other exercise facility to be analysed to enable decisions to be made as to which items of exercise equipment to provide.

Once the facility owner has used the produced data to, for example, maximise the availability of items of exercise equipment under the highest demand during the above peak times, the plurality of usage monitors may be removed from the items of exercise equipment. Thus, the plurality of usage monitors may be used on a temporary basis on standard exercise equipment, reducing the cost and inconvenience of the service. The removed plurality of usage monitors may then be used in another facility.

Alternatively, the plurality of usage monitors may be integrated into the items of exercise equipment and used on a permanent basis to provide ongoing feedback to the facility owner.

Further variations and modifications may be made within the scope of the invention herein disclosed.

The invention claimed is:

1. A method of monitoring the use of exercise equipment at an exercise facility, having a plurality of items of exercise equipment, the method comprising the steps of: providing a plurality of usage monitors, each usage monitor associated with an item of exercise equipment and operable to detect whether the respective item of exercise equipment is being either or both operated and occupied at a given time, the monitor being operable to determine whether the item of exercise equipment is being occupied independently of whether it is being operated; monitoring the usage of the said plurality of the items of exercise equipment concurrently using the said usage monitors, and thereby calculating, for at least some of the items of exercise equipment, a measurement related to the proportion of a period of time during which one or more respective items of exercise equipment are used.

2. A method according to claim 1, wherein the calculated measurement related to the proportion of the period of time during which one or more respective items of exercise equipment are used is a measurement related to the proportion of the period of time during which the one or more respective items of exercise equipment are operated.

3. A method according to claim 1, wherein at least some of the said usage monitors are operable to detect whether a user is occupying the respective item of exercise equipment at a given time and the calculated measurement related to the proportion of the period of time during which one or more respective items of exercise equipment are used is related to the proportion of the period of time during which the one or more respective items of exercise equipment are either or both operated and occupied.

4. A method according to claim 1, wherein the calculated measurement related to the proportion of the period of time during which the one or more respective items of exercise equipment are used is a measure of the period of time during which the one or more respective items of exercise equipment are not in use.

5. A method according to claim 1, wherein the period of time is a portion of day and method comprises calculating an average of measurements taken during the same period of time on a plurality of different days.

6. A method according to claim 1, comprising the step of calculating measurement related to the proportion of a period of time during which one or more of a group of a plurality of items of exercise equipment are used, or the average proportion of the items of exercise equipment within a group which are used concurrently.

7. A method according to claim 1, wherein the calculated measurements relate to the proportion of time at least one of one or more items of exercise equipment in a group of items of exercise equipment are not used.

8. A method according to claim 1, wherein the calculated measurement is related to the available capacity of items of exercise equipment in a particular group provided in the exercise facility.

9. A method according to claim 1, wherein the calculated measurement is related to the proportion of the period of time during which the one or more respective items of exercise equipment would have been used if all of the items of exercise equipment which have usage monitors associated therewith were used for equal periods of time.

10. A method according to claim 1, wherein a calculated measurement concerns the proportion of a period of time during which items of exercise equipment at each of a plurality of locations within the exercise facility are used.

11. A method according to claim 1, the method comprising displaying a graphical representation of the proportion of a period of time that one or more items of exercise equipment are used arranged according to their location within the exercise facility.

12. A method according to claim 11, wherein the period of time is part of a day.

13. A method according to claim 12, comprising the step of changing the said period of time progressively to display usage through some or all of a day.

14. A method according to claim 1, wherein the usage monitor comprises at least one sensor and a communication interface by which the data produced by the at least one sensor is transmitted to recording apparatus.

15. A method according to claim 1, wherein the at least one sensor is operable to detect whether an item of exercise equipment is being operated.

16. A method according to claim 1, wherein the at least one sensor is operable to detect whether an item of exercise equipment is occupied.

17. A method according to claim 15, wherein the same at least one sensor is operable to detect whether an item of exercise equipment is being both occupied and operated.

18. A method according to claim 16 wherein the at least one sensor comprises a heat sensor.

19. A method according to claim 14, wherein the at least one sensor is an accelerometer, a gyroscope, a vibration sensor, a load monitor or pressure sensor.

20. A method according to claim 1, further comprising using said measurement to maximise the availability of items of exercise equipment under the highest demand during peak times.

* * * * *